United States Patent
Woo

(10) Patent No.: US 6,379,295 B1
(45) Date of Patent: Apr. 30, 2002

(54) TREATMENT OF AFFLICTIONS, AILMENTS AND DISEASES

(76) Inventor: Gilson Woo, 19708 Balan Rd., Rowland Heights, CA (US) 91748

( * ) Notice: Subject to any disclaimer, the term of this patent is extended or adjusted under 35 U.S.C. 154(b) by 0 days.

(21) Appl. No.: 09/570,510

(22) Filed: May 13, 2000

Related U.S. Application Data

(63) Continuation-in-part of application No. 08/939,429, filed on Sep. 26, 1997, now abandoned.

(51) Int. Cl.⁷ .............................. A61N 1/00; A61B 19/00
(52) U.S. Cl. ........................................ 600/15; 128/898
(58) Field of Search .............................. 600/9, 13, 14, 600/15, 407; 2/115; 335/297; 128/898

(56) References Cited

U.S. PATENT DOCUMENTS

| | | | | |
|---|---|---|---|---|
| 435,343 A | * | 8/1890 | Brown | 600/13 |
| 1,164,356 A | * | 12/1915 | Kaiser | 335/297 |
| 3,658,051 A | * | 4/1972 | MacLean | 600/14 |
| 4,134,395 A | * | 1/1979 | Davis | 600/407 |
| 5,092,835 A | * | 3/1992 | Schurig et al. | 600/9 |
| 5,529,569 A | * | 6/1996 | Woo | 600/9 |
| 5,738,624 A | * | 4/1998 | Zablotsky et al. | 600/9 |
| 5,782,743 A | * | 7/1998 | Russell | 600/9 |
| 5,950,239 A | * | 9/1999 | Lopez | 2/115 |
| 6,048,302 A | * | 4/2000 | Markoll | 600/13 |
| 6,132,361 A | * | 10/2000 | Epstein et al. | 600/13 |
| 6,179,771 B1 | * | 1/2001 | Mueller | 600/13 |
| 6,267,720 B1 | * | 7/2001 | Knox et al. | 600/15 |

FOREIGN PATENT DOCUMENTS

| | | | | |
|---|---|---|---|---|
| DE | 19544475 A1 | * | 11/1995 | A61N/2/08 |
| FR | 2583292 A | * | 12/1986 | A61N/1/42 |
| GB | 2224940 A | * | 5/1990 | A61N/1/16 |
| RU | 2090220 | * | 9/1997 | A61N/2/08 |

* cited by examiner

*Primary Examiner*—John P. Lacyk
*Assistant Examiner*—Nikita R Veniaminov

(57) ABSTRACT

A method and apparatus for alleviating or curing human afflictions, ailments and diseases holistically by application of magnetism. A north pole surface of a magnet is applied to a portion of the head, about 160 square inches, of a person being treated, and is maintained in contact for a time period or periods in accordance with total flux applied for the afflictions or ailments being treated. The magnet is maintained in contact for a time period or periods sufficient to elicit holistic effect of alleviation or cure and to detect ailments and cure in progress or a balanced treatment point. Magnet is being configurated to accommodate the area being treated and having appropriate total flux.

24 Claims, 2 Drawing Sheets

TREATMENT OF AFFLICTIONS, AILMENTS AND DISEASES

RELATED APPLICATION

This application is a continuation-in-part of application Ser. No. 08/939,429 filed Sep. 26,1997 now abandoned by Gilson Woo, for the Title of TREATMENT OF AFFLICTIONS, AILMENTS AND DISEASES.

BACKGROUND OF THE INVENTION

This invention is a result of a series of findings in my research for magnetic treatment since 1980 from which a method for holistic therapeutic effect of entire body by application of magnetism only to the hands of patient was already patented by U.S. Patent Office under the title of Treatment of Ailments, Afflictions and Diseases and the respective Patent number is U.S. Pat. No. 5,529,569 Jun. 25, 1996.

The present invention is directed to a method of applying magnetism only to the head of patient for holistic effect of entire body. The conventional method is holistically effective and applicable to all ailments of human body for concurrent treatment utilizing meridians of Oriental medical theory. However, the head application is more effective with faster healing and less treatment time is required. The conventional method utilizes only hands of person and the present invention utilizes only head of person in magnetic application.

This is a method of pain relief and cure for holistic effect of entire body by applying negative magnetic flux, North pole, only to the head portion of the body of the person treated, applying the principles of the Oriental Medicine utilizing the body's meridians known as pathway of life energy of the human body.

This method involves 4 meridians and 64 acupoints that are being disposed through the head, which are Governing Vessel of 10 acupoints, Bladder of 18 acupoints and Gall Bladder of 34 acupoints and stomach of 2 acupoints, whereas only hand meridians are being utilized in the referenced prior art of the two-hand method of holistic magnetic therapy. This method is extremely effective in relieving pain, inflammation and distress associated with neural/nerve systems and especially chronic ailments related with the complicated energy system.

When magnetic fluxes are applied to the head in the designated area as shown in the diagram of FIG. 1 of drawings for therapeutical effect, brain cells are energized and three (3) vital elements of body function are affected, i.e. meridians life energy pathway, brain the body's main control center and central nervous system. These important elements including brain control functions are being stimulated or restored instantly, upon application of magnetism to the head, to elicit holistic therapeutical effect of entire body, thus breathing, circulation and energy flow are improved to help body heals fast and relieves pains effectively, which are all observable and verifiable at sight. This method enables body to sense responses from ill parts (location) and cure in progress in same way as two-hand method of the referenced prior art, and sensing response is much clearer with far less treatment time and faster healing, whereas note there is no response being occurred or detected from the healthy body with no ailments by application of magnetism.

This phenomenon is believed to be some form of reaction of brain sick memory recall in response to the magnetic application and further to indicate that, when body is in sickness, pathway of life-energy (meridian) and sensory neurons of the nervous system are being hindered by some form of blockage and, when the flow is stimulated by magnetic flux, the flow hindrance causes responses and symptoms and, when the body is in health, the pathways are all clear and wide open for free flow thus causing no response or symptom even under magnetically stimulated condition in energy flow and neural transmission. An evidence to support this fact is that, when pain and ailment are cured by magnetic flux, all such responses and symptoms are gone and disappeared.

Magnets and magnetism have heretofore been utilized in the treating of human disease and afflictions. Any magnet configurated and sized to cover substantially the treatment area of the head can be used for this method as long as it produces a sedative and healing effect in a range of 30 to 250,000 total flux and the north pole surface is flat and smooth for good contact to the head. Total flux of up to 5,000 is believed to be ideal for pain control and management of sedative effect and total flux of above 5,000$\phi$ is believed to be good for healing cure effect.

In comparison with the referenced method of prior art, this method of utilizing head is more beneficial in many ways: more effective—higher ability in cure, less treatment time, faster healing, easy of balanced treatment, natural energizing effect (rejuvenated), etc. Magnetic application in terms of alternative medicine or natural energy medicine has been widely recognized in the Western in recent years although this has been primarily an Oriental practice.

Many innovative methods of magnetic treatment have been introduced, yet there is much left to be done for improvement.

Therefore, a general object of the present invention is to provide treatment for a wide variety of ailments and diseases for holistic effects, except for those requiring surgical treatment.

An object of the present invention is to provide such a method which utilizes magnetism applied to a portion of the head of a person, thus to provide concurrent treatment of a plurality of ailments and afflictions of the entire body for holistic effect.

An object of the invention is to provide such treatment utilizing magnetism in simplified methods that can be practiced without specialized professional knowledge.

An object of the invention is to provide such methods that provide recovery from fatigue and which provide energetic, vigorous feelings.

An object of the invention is to provide such methods that provide substantial cures, relief of pain and rapid healing.

An object of the invention is to provide such methods that provide breathing control and/or improved circulation of the blood of the person to allow an optimum condition of the body systems.

An object of the invention is to provide methods and techniques of treatment utilizing magnetism, independently of meridians or acupuncture points according to Oriental medicine.

An object of the invention is the provision of such a method which is economical and effective.

An object of the invention is the provision of such methods which, properly utilized, are safe and involve no harm to a patient and no adverse reaction or sequelae.

An object of the invention is the provision of such methods which involve the effecting of a balance of the energy systems of the body, in accordance with Oriental medicine theories, in treating ailments and applications.

SUMMARY OF THE INVENTION

The foregoing object and advantages, as well as others which will be apparent from the specification, are achieved by a method for treating and alleviating human afflictions, ailments and diseases by the application of magnetism to a person being treated. A north pole surface of a magnet is applied to the person, only to a portion of the head. Contact with magnet is maintained for a sufficient time period or periods to provide substantial alleviation or cure. The magnetic strength or total flux applied to the head may typically be from about 30 to about 250,000 total flux. The magnet may be maintained in contact with the person for a time period sufficient for the eliciting of substantial alleviation or cure. Magnet means are provided for application to the portion of the head of a person being treated, with a north pole surface of the magnet means configurated to engage the portion or the area of the head of the person.

DESCRIPTION OF THE PREFERRED EMBODIMENT

According to the present invention magnet or magnets are applied to the head of the person being treated. The method of head magnetic treatment involves application of magnetism by attaching a magnet directly to the designated treatment area of the head only to elicit holistic therapeutical effect of entire body. In utilizing the method, where affliction or chronic ailment is treated, the head is subjected to the magnetic treatment according to the invention.

Figure 1:
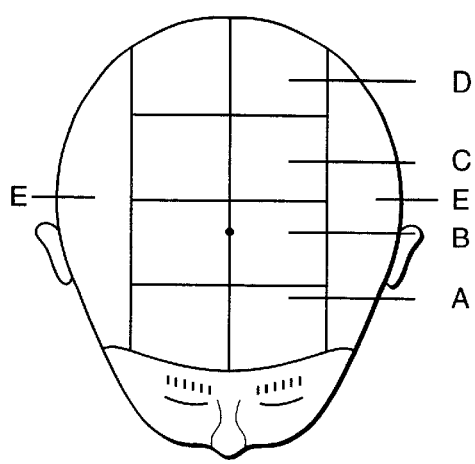
FIG. 1 is a perspective view showing whole designated treating regions utilized in the invention in the application of magnet means to the head of a person.
Figure 2:
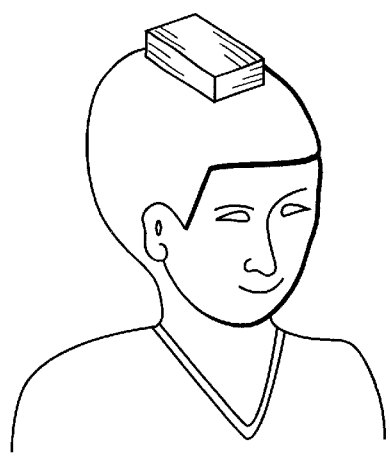
FIG. 2 is a perspective view showing the application of head of a person to magnet means.

The method is the most effective and powerful method of holistic treatment. The affliction, ailments and diseases of the entire body of a person may be treated concurrently by application of magnet means to the area of the head of the person. In this method, magnets are applied directly to the designated area of the head of a patient. A particular area of the head is being designated for holistic therapeutical effect and its size is about 160 square inches, 16 inches long and 10" inches wide, as shown in FIG. 1. The designated area of the head covers from eyebrow line in 10" wide all the way through the median line of the head to the occipital hairline in 16" long. The governing vessel meridian is disposed through the median line of the head which is the intermediate line of the designated area, and bladder and gall bladder meridian are disposed on each side of the median line of the head, and stomach meridian is disposed in the forehead area near the frontal hairline. Thus, there are four meridians and 64 acupoints that are disposed in the designated area involving the cranial head method of holistic treatment. However, the 64 acupoints in the area are normally used by acupuncture technics to treat only the ailments associated with head, eye, nose, teeth, nasal cavity, mouth, mental sickness, insomnia, neck stiffness, hemorrhoids and constipation, etc., and they provides no means of holistic effects of entire body. But by applying magnetism to the area as a whole in accordance with the invention provides an effective means of holistic therapeutical effect of whole body.

In order to elicit such an holistic therapeutical effective and balanced treatment, the designated treatment area of the head may be divided, as shown in FIG. 1, into 6 treating regions such as A, B, C, D, E and F, respectively for frontal part, top part, upper back part, lower back part, left side part and right side part of the head.

These regions of A, B, C, D, E and F of the head are treated either separately or in group or all together as a whole. Thus, by applying magnet means to the designated area of the head, afflictions of all ailments and diseases of entire body are treated concurrently and holistically.

Figure 3:
FIG. 3 is a perspective view of a person undergoing application of magnet means to the head.
Figure 4:
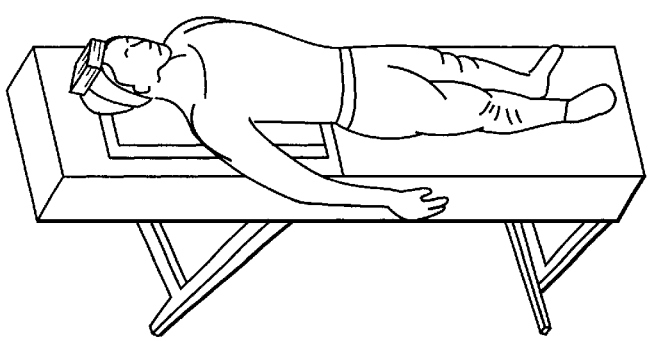
FIG. 4 is a perspective view showing a preferred manner of utilizing the invention in the application of magnet means to the head of a person, with the person in a recline, prone position.
Figure 5:
FIG. 5 is a perspective view showing the application of a north pole surface of a magnet of generally head shaped configuration encased in a helmet to the head of a person.
Figure 6:
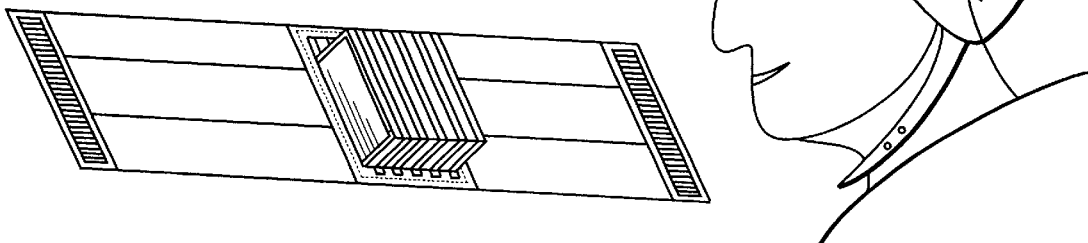
FIG. 6 is a perspective view showing a wrap around style band made of elasticized material with Velcro fasteners for the application of a north pole of a magnet of rectangular configuration to the head of a person.
Figure 7:
FIG. 7 is a perspective view showing a partial treatment of all regions concurrently, for a balanced treatment.
Figure 8:
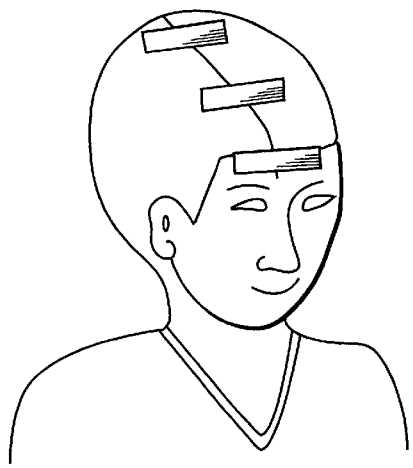
FIG. 8 is perspective view showing the application of the median line of the head, Governing Vessel Meridian.
Figure 9:
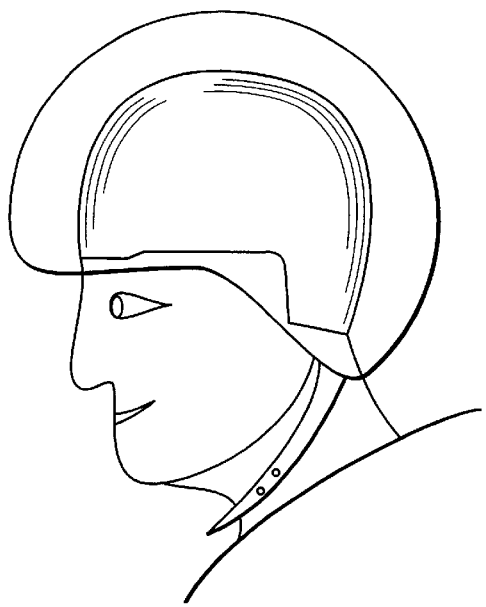
FIG. 9 is a perspective view showing a treatment of all regions together concurrently.
Figure 10:
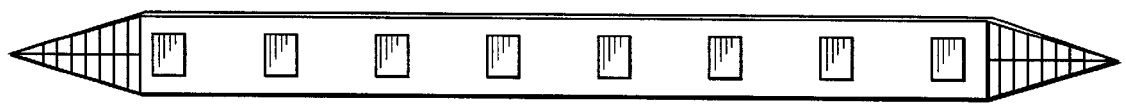
FIG. 10 is a perspective view showing a head band utilized for a partial treatment of regions in group concurrently.

The method of head treatment by utilizing magnet or magnets are described as follows; Magnet or magnets are attached directly to the head in the designated area, as shown in FIGS. 2, 3, 4, 5, 7, 8 and 9 of the drawings. The magnet or magnets may be applied to the entire area of the head concurrently, as shown in FIGS. 5 and 9 of the drawings, or partially by region at a time, as shown in FIG. 3 of the drawing, consecutively or at intervals, one by one with an equal amount of treatment time, or partially by regions in groups at a time, as shown in FIG. 8 of the drawings, with an equal amount of treatment time, or partially by all regions together concurrently as shown in FIG. 7 of the drawings. In utilizing partial treatment by region at a time, or regions in group or altogether, balanced treatment should be practiced in the following manner. For partial treatment by each region at a time; The front, top, lower back, upper back, left side and right side part of the head should preferably be treated separately, one by one, at intervals of 10 hours, in that order, with an equal amount of treatment time. For partial treatment by regions in 3 groups: First, magnet is applied to the front part, section A, then top part, section B, consecutively, in that order, with an equal amount of treatment time for a balanced treatment. At interval of 10 hours, lower back part, section D, is treated first, then upper back part, section C, consecutively, in that order, with an equal amount of treatment time.

At interval of 10 hours, side parts, section E and F are treated consecutively, in either order, with an equal amount of treatment time for a balanced treatment. For partial treatment by regions in 2 groups: All sections of A,B,C and D along the median line of the head are treated together first, then, at same interval or consecutively, section E and F on each side of the head are treated together second, or vice versa, with an equal amount of treatment time for a balanced treatment.

For partial treatment by all regions together concurrently: All treating regions of A,B,C,D,E and F of the head is treated together, concurrently.

Partial treatment may be practiced with any number of magnets sized more than ¼" in diameter. Number of magnets used is determined by size and total flux of the magnet based on repelling and pulling power. In case of utilizing single magnet: Number of consecutive treatment required for each region of the head is determined by size of the magnet used in diameter, for example, if the diameter of the magnet used is 2" and the region "A" is 4" long, then divide region length of 4" by magnet length of 2" gives 2 treatments needed to treat total length of region "A" of the head. In case of utilizing multiple magnets for partial treatment of a region or multiple regions together: Magnets are placed and spaced apart one another at an equal distance through out a region or multiple regions, as shown in FIG. 7 of the drawings, so that magnets are placed evenly through out entire area of the head. Thus, all parts of the head is treated equally of total flux for balanced treatment.

In applying magnetism to the head of a patient, the magnets are preferably configured and sized to cover partially or substantially the regional area of the head, and preferably to cover. substantially the entire regions of the head of the patient. Only the north pole of a magnet is applied.

In utilizing the area in the regions in application to the head of a patient, it is typically and ordinarily necessary, in order to avoid a imbalance treatment in accordance with the Oriental medical theory, to apply magnet or magnets with an equal total flux for each and all treating area of the regions with an equal amount of treatment time for a balanced treatment. And, in addition, the balanced concept should also be applied by using the median line of the head which divided the head into a half, left and right, in order to avoid an imbalance condition of the body systems. Accordingly, when applying magnet or magnets along the median line of the head, always place the center of the magnet on the median line of the head, as shown in FIG. 8 of the drawings, regardless of size, so that intermediate line of the magnet is aligned with the median line of the head, Governing vessel meridian line, for equal distribution of magnetic flux for both side of the head, and this practice should be applied to all magnet sizes used under this cranial head method of magnetic application. Any magnet, permanent or electromagnet, may be utilized.

Typically, a flat magnet is employed, thus to provide well contact and substantially equal magnetic flux over the area of the head. In applying magnets to the head of a patient, it is desirable that magnets of equal size and total flux are applied evenly to whole area of the head and, in addition, for treatment by subregion of the head equal time of treatment should be practiced for a balanced treatment.

The magnet may have any configuration appropriate to the area to which it is to be applied, such as square, rectangular, circular, oval, disc or bar. The size of the magnet should be such as to cover the entire regions of the head or only the subregions of the head or only a part of the subregions and the median line of the head, at least more than ¼" inch diameter. Practically, any size appropriate for the head is usable, however, the range of the magnet size preferred for this head method is from ¼"×¼" to 10"×16". Any magnet within this range of size can be effectively used.

In applying magnet means to the head, magnet or magnets are attached to the head skin in the designated area of the head by using headgear, elastic band, cap-helmet-shaped wrapper or cover with Velcro fasteners for well contact, as shown in FIGS. 5, 6, 9 and 10 of the drawings.

Elastic band may include wraparound belts to securely hold the magnets sewn-in or encased in fabric lining, or adjustable Velcro type fasteners. The magnet is positioned so that it is not readily removable or separable from the skin of the head of the patient in order to be properly effective.

Magnets should be contacted well to the skin of the head so that no gab between magnet and skin is allowed. Therefore it is imperative that hair be moved from the contact area as much as possible before attaching magnets to the head skin. As disclosed in the prior art of the two-hand method, the closer contact to the skin for magnet the better for effectiveness and, on the contrary, the farther from the skin the lesser effective.

The method is applicable for all afflictions, ailments and diseases. As stated, it is the best and most effective method according to the invention, and serves to treat concurrently various or all afflictions and ailments of the entire body of a person. The method also serves to energize the person and relieve tiredness.

Effectiveness and applicability of the method are all observable at treatment site and easily verifiable instantly by patient during treatment in same way as prior art of two-hand magnetic method.

Treatment may begin with a relatively low power magnet, with successive application of magnets of increasing strength in accordance with the progress, response and feeling of the patient relative to relief. Typically, response is felt after 15 minutes, and within 30 minutes the patient can sense a cure in progress and a good feeling. Fifteen to ninety minutes of application is the optimum period for most effective treatment of most ailments or diseases.

The treatment time is typically 15 to 180 minutes, typically once or twice daily at interval of about 10 hours.

The north side of the magnet is applied directly to the area of the head and is left in place for 15 to 180 minutes. Pain is typically then gone.

Treatment commences upon application of the magnet and typically extends from 15 to 180 minutes, one or two times per day, at intervals of about 10 hours.

At the end of each treatment, the magnet or magnets are removed. Most ailments or diseases are cured or greatly alleviated with one or two treatments. Treatment may be repeated until complete cure is effected. The treatment may be repeated at intervals in accordance with need and progress. For relatively serious or long-term ailments, treatment may extend for many days, and even for a few months or more. In case of long-term treatment by utilizing a partial treatment method, treatment should be repeated in same order with intervals, as described earlier, so that all regions of the head are treated in each and every repeated session of treatment. The effectiveness of treatment extends for about twelve hours after removal of the magnet or magnets. Relatively simple or minor ailments or complaint is cured with one or two treatment.

The criterion used in this invention for therapeutic effectiveness and operativeness was "Did all pains of patient relieved concurrently from whole body within 15 minutes to two hour of each treatment session and did any side effect occurred or accompanied and did patient detect ailment and progress of cure and did patient feel energized".

Applying north pole of the magnet to the designated area of the head of the patients, in accordance with the invention, relieves all pains of whole body concurrently, regardless of cause and location, showing holistic total effect for whole body of the patient. Of various medical treatments, utilizing magnet means to the head in accordance with the invention is found to be the most effective to cope with pains and affliction. In practice of this holistic treatment, cause, location and names of ailments involved are not considered as important factors for treatment because all pains and afflictions associated with various ailments of whole body including chronic diseases are treated holistically and concurrently with excellent result of pain relief and cure, which are all observable and verifiable at site while treated within 15 minutes to three hours with no waiting time period for the treatment result, unlike conventional method. And in addition, patients can detect own ailments and cure in progress and final result as well by symptoms occurred in response to the magnetic application to the head, and patients treated become energized and feel a power or strength in arms and wrists, especially when awaked in the morning.

Introduced below shows a typical example of the holistic total treatment for afflictions of all ailments of entire body for which the magnet device and the method were utilized—male patient, 39 years old, who was suffered for one day from food poison accompanied by laxity, vomiting, dehydration, severe stomach ache, headache, pain in the extremities, high fever and completely exhausted as he could not eat anything all day, was treated with this head method by utilizing a magnet of 1.5"D xI"H with about 5,000 total flux for two full sessions in one day at interval of 10 hours. Laxity stopped and all pains and symptoms of the afflictions were gone and cured completely with only three sessions in two days.

The patient was able to eat next morning and went to work in full recovery without any feeling of weakness. Follow-up confirmed no recurrence of any symptoms of food poison. Normally, it is impossible to cure a severe food poison in two days with the conventional method. In proceeding according to the invention, the person or patient is preferably in a prone position, as shown in FIG. 4 or seated position for the application of magnetism. Magnet means may be applied to the head while the person is in a standing, sitting, or recline position, as indicated in FIGS. 3 & 4.

During the treatment, afflictions, ailments and diseases of a person are detected and sensed by the responses and symptoms of the person in response to the application of the magnetism in same way as prior art of two-hand magnetic method. The patient may sense responses involving complex symptoms, such as pain, strain, tightness, itch, warmth, coldness, etc. Such symptoms may be mixed and continue until the spot is cured or relieved. The cure in progress is sensed by the person during the application of magnetism in accordance with the invention.

The response or reaction of the patient to the head treatment may involve the entire body. Symptoms occur from all diseased or afflicted areas of the body of the patient, and symptoms are usually continued until all ailments and diseases are greatly alleviated or cured. When all ailments are cured, all symptoms and responses are completely gone and this happens only when there is no ailment in the body. Thus there is no symptom or response occurring from healthy body even under magnetic application to the head or hands. Such phenomenon is all observable and verifiable instantly by patient at treatment site while in treatment. As stated earlier, after application of the magnet for an appropriate time, the patient senses a response and therapeutical effect of cure in progress.

For internal illnesses or ailments or chronic diseases, after 15 minutes of application of the magnets to the head, a response or reaction occurs in the patient, and the patient can sense a good response and active curing in 15 to 60 minutes of treatment. After approximately 90 minutes of application of the magnet, the response or reaction of the person's body gradually diminishes, the patient's body becomes relaxed, and a feeling of well-being permeates the patient's body. This point in time of a treatment may be called as a balanced treatment point. When balanced point is reached through the course of a treatment whole body becomes relaxed and then all pains and afflictions are gone with a feeling of well being. At this very moment treatment should be stopped immediately—magnets should be removed from the head skin, otherwise, the balance point may be reversed by over-treatment with a result of less effectiveness and a possible side effect.

Therefore, in accordance with the balance concept of Oriental medical theory, the point of being relaxed, easy state of human body occurring during a treatment is believed to be the exact point of a well balanced state of harmony in body systems in treatment. The magnet may typically be applied for 15 to 180 minutes and for not more than 180 minutes of a maximum balanced point, in order to prevent over-balanced treatment. Such balanced point in treatment is also dependent upon and is affected by factors including total flux, distance between magnet and skin, and condition of ailment and thereby each person might have a different balanced point. However, in most cases, the balance points of treatment are within a range of 15 to 180 minutes. Therefore, the magnets may be applied within the specified time period needed to produce therapeutic effect and the following schedule may preferably be observed in the head treatment:

Treatment: 15–180 minutes

Resting time: 10 hours

Frequency: 1–2 times daily/ whenever pain occurs

In application of magnetism to the head of person, virtually all magnet, permanent and electromagnet, including weak magnets may be used and are all effective, whereas only relatively strong magnets with a total flux of more than 5,000φ are utilized in the referenced prior art of two-hand method. Permanent magnets are preferred for economic reasons, but electromagnets can be utilized to advantage because their power can be varied or desired, within design limitations. The range of total flux for magnets used is about 30–250,000 and such total flux is measured at 0.0019" from the north pole surface of the magnet means. The size of the magnet may typically be ¼"×¼" to 10"×16".

The effectiveness and curative results increase with increase of flux density (gauss) and total flux of the magnet applied to the person. The total flux applied to the patient is considered to be of key importance.

The following formula sets forth the relationship between total flux, flux density and magnet pole area:

$\phi = BA$

Where: $\phi$ = total flux $B$ = flux density in gauss $A$ = area

Magnetic application to the head has been found to be very safe, however, only for precaution, magnets should not be utilized in treating infants, pregnant women and person with heart pacemaker or metal implanted.

Thus there has been shown and described a novel treatment of afflictions and ailments with magnetism which fulfills all the objects and advantages sought therefore.

Many changes, modifications, variations and other uses and applications of the subject invention will, however, become apparent to those skilled in the art after considering this specification together with the accompanying drawings and claims.

All such changes, modifications, variations and other uses and applications which do not depart from the spirit and scope of the invention are deemed to be covered by the invention which is limited only by the claims which follow.

What is claimed is:

1. A method of treating and alleviating human afflictions, ailments and diseases holistically by application of magnetism to a plurality of treating regions of the head of a person being treated, the method comprising the steps of:

providing a magnet having at least one north pole surface adapted for application to the plurality of treating regions of the head; designating at least six treating regions of the head having a total size of about 160 square inches, covering about 10"×16" of a head region from an eyebrow line through a head median line to an occipital hairline;

applying at least one north pole surface of the magnet to at least one of the plurality of treating regions of the head, the magnet having a size of ¼"×¼" to 10"×16" and a shape appropriate to cover at least part of one of the treating regions of the head; and maintaining the magnet in contact with at least one of the treating regions of the head for a period of 15 to 180 minutes to treat and relieve afflictions, wherein a total flux of the magnet applied to the at least one of the treating regions of the head is in a range from about 30–250,000.

2. The method of claim 1, further including the step of repeating the application of the magnet for at least one additional period of time.

3. The method of claim 1, further comprising repeating the treatment at an interval of about 10 hours at least once in a 24 hours time period.

4. The method of claim 1, wherein: plurality of treating regions of the head include a frontal region, a parietal region, left and right temporal regions, and upper and lower parts of occipital region, and further including applying the magnet to each of the plurality of treating regions.

5. The method of claim 4, wherein applying the magnet to each of the plurality of treating regions of the head is performed in the order of the frontal region, the parietal region, the lower occipital region, the upper occipital region, the left temporal region and the right temporal region.

6. The method of claim 4, wherein applying the magnet to each of the plurality of treating regions of the head is performed in the order of the frontal and parietal regions together, the lower occipital and upper occipital regions together, and the left and right temporal regions last, or in reverse order.

7. The method of claim 4, wherein applying the magnet to each of the plurality of treating regions of the head is performed in the order of the frontal, parietal, lower and upper occipital regions together, and the left and right temporal regions last, or in reverse order.

8. The method of claim 1, wherein applying the magnet first to one selected area of the treating regions of the head of the person and wherein applying the magnet then to another selected area of the treating regions.

9. The method of claim 1, further including applying the magnet to multiple of said plurality of treating regions of the head of a person concurrently.

10. The method of claim 1, further including applying the magnet to all of said plurality of treating regions of the head of a person concurrently.

11. The method of claim 1, further including applying the magnet partially to at least one of the plurality of treating regions of the head of a person.

12. The method of claim 1, further including applying the magnet partially to multiple of said plurality of treating regions of the head of a person concurrently.

13. The method of claim 1, further including applying the magnet partially to all of said treating regions of the head of a person concurrently.

14. The method of claim 1, wherein a total flux of the magnet applied to each one of the plurality of treating regions of the head of the person is substantially equal.

15. The method of claim 1, further comprising applying multiple magnets to the treating regions of the head concurrently by disposing the magnets evenly, spaced apart at an equal distance regions of the head so that all parts of the treating regions of the head of the person are treated equally with a total magnetic flux for a balanced treatment.

16. The method of claim 1, further comprising placing a center of the magnet on a median line of the head so that an intermediate line of the magnet is aligned with the median line of the head to provide an equal distribution of a magnetic flux for a balance treatment.

17. The method of claim 1, further comprising applying additional magnets having substantially equal total flux to the treating regions of the head of a person for a balanced treatment.

18. The method of claim 1, further comprising applying the magnet consecutively or at intervals to selected treating regions of the head of the person for equal time periods for a balanced treatment.

19. The method of claim 1, further comprising substantially covering the entire plurality of treating regions of the head of the person with the north pole surface of the magnet.

20. The method of claim 1, further comprising substantially covering each of the plurality of treating regions of the head of the person with the north pole surface of the magnet.

21. The method of claim 1, further comprising partially covering each of the plurality of treating regions of the head of the person with the north pole surface of the magnet.

22. The method of claim 1, further including: disposing retaining means for holding the magnet to the head to provide effective contact of the north pole surface of the magnet with the head.

23. The method of claim 1, further comprising: contacting the magnets directly to the treating regions of the head by using a headgear, a band, a wrapper or a cover with magnets sewn-in or encased in any shape of form appropriate to fit the treating regions of the head of a person.

24. The method of claim 23, wherein the headgear, band, wrapper or cover for contacting the magnets to the treating regions of the head of a person are made with any material that is safe to the head and appropriate for fabrication.

* * * * *